(12) United States Patent
Mourran

(10) Patent No.: US 12,731,708 B2
(45) Date of Patent: Sep. 8, 2026

(54) CORROSION-RESISTANT PERMANENT MAGNET FOR AN INTRAVASCULAR BLOOD PUMP

(71) Applicant: Abiomed Europe GmbH, Aachen (DE)

(72) Inventor: Claudia Mourran, Aachen (DE)

(73) Assignee: Abiomed Europe GmbH, Aachen (DE)

(*) Notice: Subject to any disclaimer, the term of this patent is extended or adjusted under 35 U.S.C. 154(b) by 917 days.

(21) Appl. No.: 17/773,924

(22) PCT Filed: Nov. 10, 2020

(86) PCT No.: PCT/EP2020/081608
§ 371 (c)(1),
(2) Date: May 3, 2022

(87) PCT Pub. No.: WO2021/094297
PCT Pub. Date: May 20, 2021

(65) Prior Publication Data

US 2022/0384070 A1 Dec. 1, 2022

(30) Foreign Application Priority Data

Nov. 12, 2019 (EP) .................................... 19208712

(51) Int. Cl.
*H01F 1/057* (2006.01)
*A61M 60/416* (2021.01)
*H01F 7/02* (2006.01)

(52) U.S. Cl.
CPC ......... *H01F 1/0572* (2013.01); *A61M 60/416* (2021.01); *H01F 1/0577* (2013.01); *H01F 7/02* (2013.01)

(58) Field of Classification Search
None
See application file for complete search history.

(56) References Cited

U.S. PATENT DOCUMENTS 4,497,890 A 2/1985 Helbert
5,154,978 A 10/1992 Nakayama et al.
(Continued)

FOREIGN PATENT DOCUMENTS

CN 109891533 B 1/2022
EP 0984460 A2 * 3/2000 ........... H01F 41/026
(Continued)

OTHER PUBLICATIONS

Abstract Translation of JP H6140226 A (Year: 1994).*
(Continued)

*Primary Examiner* — Kevin M Bernatz
(74) *Attorney, Agent, or Firm* — Botos Churchill IP Law LLP

(57) ABSTRACT

This invention is directed to a corrosion-resistant permanent magnet, to a method for producing a corrosion-resistant permanent magnet, and to an intravascular blood pump comprising the magnet. The magnet is surrounded by a composite coating, the composite coating comprising, in the order recited, a first metal oxide layer, a metal layer, a second metal oxide layer, a linker layer, and a layer formed from poly(2-chloro-p-xylylene). In an alternative embodiment, a further metal layer and, optionally, a further metal oxide layer may be provided between the second metal oxide layer and the linker layer. In a further alternative embodiment, the metal layer may be omitted, and a further layer structure comprising at least one metal oxide layer, a linker layer, and a layer formed from poly(2-chloro-p-xylylene) may be provided instead.

14 Claims, 4 Drawing Sheets

(56) References Cited

U.S. PATENT DOCUMENTS

Figure 1:
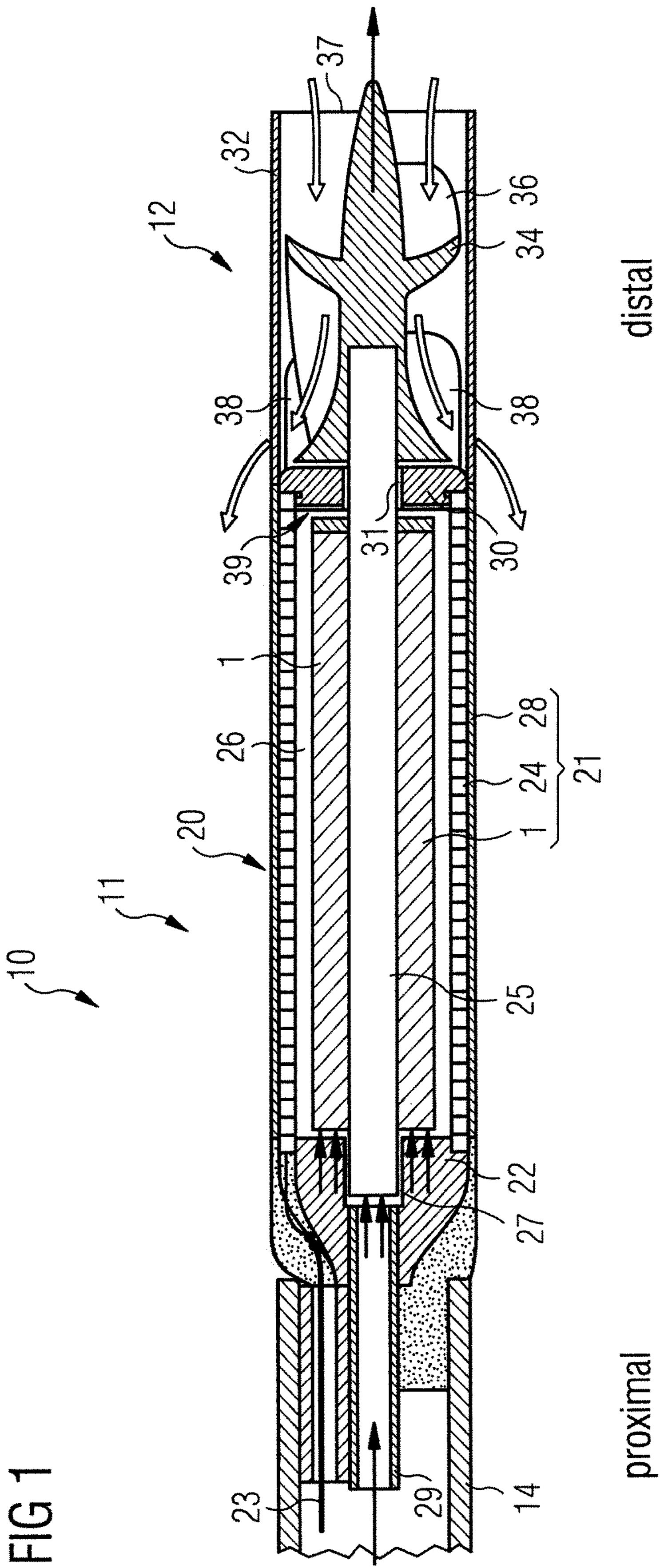

| | | | | |
|---|---|---|---|---|
| 6,062,679 | A | 5/2000 | Meyer et al. | |
| 6,176,848 | B1 | 1/2001 | Rau et al. | |
| 9,028,981 | B2 | 5/2015 | Yoshida et al. | |
| 2003/0041920 | A1* | 3/2003 | Hoshi | H01F 41/026 148/122 |
| 2008/0185174 | A1 | 8/2008 | Bedinger et al. | |
| 2008/0200750 | A1 | 8/2008 | James | |
| 2009/0112312 | A1 | 4/2009 | Larose et al. | |
| 2011/0039050 | A1 | 2/2011 | Hogg et al. | |
| 2012/0182102 | A1 | 7/2012 | Wang | |
| 2014/0017488 | A1* | 1/2014 | Haack | C23C 16/50 428/447 |
| 2016/0088756 | A1 | 3/2016 | Ramadas | |
| 2019/0311850 | A1* | 10/2019 | Siess | H01F 41/026 |
| 2021/0098166 | A1* | 4/2021 | Mourran | A61M 60/422 |

FOREIGN PATENT DOCUMENTS

| | | | | |
|---|---|---|---|---|
| EP | 3156234 | A1 | 4/2017 | |
| EP | 3319098 | A1 * | 5/2018 | H01F 7/02 |
| EP | 3567619 | A1 | 11/2019 | |
| JP | H02208904 | A | 8/1990 | |
| JP | H0341703 | A | 2/1991 | |
| JP | 06140226 | A * | 5/1994 | H01F 1/0572 |
| JP | H07170064 | A | 7/1995 | |
| JP | H09289108 | A | 11/1997 | |
| JP | H1070114 | A | 3/1998 | |
| JP | H10290138 | A | 10/1998 | |
| JP | H11157077 | A | 6/1999 | |
| JP | 2000256878 | A | 9/2000 | |
| JP | 2001517102 | A | 10/2001 | |
| JP | 2002212750 | A | 7/2002 | |
| JP | 2002523147 | A | 7/2002 | |
| JP | 2004064895 | A | 2/2004 | |
| JP | 2005210095 | A | 8/2005 | |
| JP | 2006351946 | A | 12/2006 | |
| JP | 2010518627 | A | 5/2010 | |
| JP | 2011009627 | A | 1/2011 | |
| JP | 2012119338 | A | 6/2012 | |
| JP | 2013098447 | A | 5/2013 | |
| JP | 2013255792 | A | 12/2013 | |
| JP | 2016134454 | A | 7/2016 | |
| JP | 2018504215 | A | 2/2018 | |
| JP | 2019022735 | A | 2/2019 | |
| JP | 2020503083 | A | 1/2020 | |
| JP | 2021523570 | A | 9/2021 | |
| WO | 9737698 | A1 | 10/1997 | |
| WO | 0010622 | A1 | 3/2000 | |
| WO | 0206562 | A1 | 1/2002 | |
| WO | 2005052960 | A2 | 6/2005 | |
| WO | 2015190409 | A1 | 12/2015 | |
| WO | 2016118735 | A1 | 7/2016 | |
| WO | 2018082987 | A1 | 5/2018 | |

OTHER PUBLICATIONS

Office Action from corresponding Korean Patent Application No. 10-2019-7015775 dated Jan. 11, 2023, (13 pp.).

"Organosilicon Monomers and Polymers", 1st edition, Organosilicon Writing Group, Chenguang Chemical Research Institute, Chemical Industry Press (Dec. 1986).

Office Action issued in Chinese Patent Application No. 2021-11618297.4, mailed Jul. 26, 2024, 30 pages.

International Search Report and Written Opinion for PCT Application No. PCT/EP2017/077334, dated Feb. 2, 2018 (8 pages).

International Search Report and Written Opinion for PCT Application No. PCT/EP2020/081608, dated Jan. 15, 2021 (12 pages).

The Extended European Search Report for European Patent Application No. 19208712.0, dated May 12, 2020 (5 pages).

First Office Action issued in Japanese Patent Application No. 2022-527092, mailed Nov. 26, 2024, 6 pages.

Office Action in corresponding Japanese Patent Application No. 2019-523602 dated Apr. 26, 2022 (8 pp.).

Office Action in corresponding Japanese Patent Application No. 2019-523602 dated Sep. 28, 2021 (16 pp.).

"Drive Performance and Design Application of Large Gap Magnetic Drive System", 1st Edition, Xu Yan, pp. 9-10, 13, Coal Industry Press.

Chinese Office Action dated Oct. 26, 2023 for CN Appln. No. 202111618297.4.

Encyclopedia of Chemical Engineering vol. 3, 1st Edition, Cutter Materials—Power Generation, p. 907, Chemical Industry Press.

Introduction to Materials Chemistry, 1st Edition, Deng Qigang et al., p. 259, Harbin Institute of Technology Press.

Office Action from Japanese Patent Application No. 2022-135033 dated Sep. 13, 2023 (10 pp.).

Office Action from Korean Patent Application No. 2022-7019221 dated Apr. 10, 2024 (10 pp.).

Office Action issued in Japanese Patent Application No. 2024-115481 dated Apr. 30, 2025 (8 pp.).

Office Action from corresponding European Application No. 20197483.9-1212 dated Jan. 1, 2023 (9 pp.).

Office Action issued in U.S. Appl. No. 18/610,361, dated Jul. 28, 2026.

* cited by examiner distal
proximal
10
11
12
20
21
22
23
24
25
26
27
28
29
30
31
32
34
36
37
38
38
39
1
1 a)

b)

a)

b)

CORROSION-RESISTANT PERMANENT MAGNET FOR AN INTRAVASCULAR BLOOD PUMP

CROSS-REFERENCE TO RELATED APPLICATIONS

The present application is a national phase entry under 35 U.S.C. § 371 of International Application No. PCT/EP2020/081608, filed Nov. 10, 2020, published as International Publication No. WO 2021/094297 A1, which claims the benefit of European Patent Application No. 19208712.0, filed Nov. 12, 2019, the disclosures of all of which are hereby incorporated by reference in their entirety.

This invention relates to corrosion protection of permanent magnets. In particular, this invention relates to permanent magnets having a protective coating rendering the magnets resistant to corrosion, and to methods for producing corrosion-resistant permanent magnets. This invention also relates to intravascular blood pumps comprising the inventive corrosion-resistant permanent magnets. While the invention is applicable to all kinds of permanent magnets, rare-earth permanent magnets are preferred, and neodymium iron boron (NdFeB) permanent magnets are particularly preferred.

Intravascular blood pumps support blood flow in a patient's blood vessel. They are inserted percutaneously into, for example, the femoral artery and guided through the body's vascular system to their destination, for example a ventricle of the heart.

A blood pump typically comprises a pump casing having a blood flow inlet and a blood flow outlet. In order to cause a blood flow from the blood flow inlet to the blood flow outlet, an impeller or rotor is rotatably supported within the pump casing about an axis of rotation, with the impeller being provided with one or more blades for conveying blood.

An exemplary blood pump is illustrated in FIG. 1. FIG. 1 is a schematic longitudinal section of an exemplary intravascular blood pump 10. The blood pump has a motor section 11 and a pump section 12 which are disposed coaxially one behind the other and result in a rod-shaped construction form. The pump section is extended by a flexible suction hose (not shown) which has, at its end and/or in its side wall, openings for the entry of blood to the pump. The end of the blood pump 10 facing away from the suction hose is connected to a catheter 14, optionally in combination with a guide wire for steering the blood pump to its destination.

The exemplary intravascular blood pump shown in FIG. 1 has the motor section 11 and the pump section 12 firmly connected to one another. The motor section 11 has an elongate housing 20 in which the electric motor 21 is housed. An electric motor has a rotor and a stator. The stator is the stationary part of the motor's electromagnetic circuit, while the rotor is the moving part. Either the rotor or the stator comprises electrically conductive windings, while the other comprises permanent magnets. Electric current flowing in the windings creates an electromagnetic field interacting with the magnetic field of the permanent magnets to generate the forces that turn the rotor. In the exemplary blood pump of FIG. 1, the stator 24 of the electric motor 21 has, in the usual way, numerous circumferentially distributed windings as well as a magnetic return path 28 in the longitudinal direction. It is firmly connected to the motor housing. The stator 24 surrounds the rotor 1 connected to the motor shaft 25 and consisting of a permanent magnet magnetized in the active direction. The motor shaft 25 extends over the total length of the motor housing 20 and protrudes distally out of the latter. There, it carries an impeller 34 with blades 36 projecting therefrom or pump blades which rotate within a tubular pump housing 32 which in turn is firmly connected to the motor housing 20.

The proximal end of the motor housing 20 has the flexible catheter 14 sealingly attached thereto. In the present disclosure "proximal" and "distal" indicate the position with respect to a physician inserting the intravascular blood pump, i.e. the distal end is at the impeller side. Through the catheter 14 there extend electrical cables 23 for power supply to and control of the electric motor 21. There additionally extends through the catheter 14 a purge-fluid line 29 which penetrates the proximal end wall 22 of the motor housing 20. Purge fluid (schematically illustrated by bold arrows) is fed through the purge-fluid line 29 into the interior of the motor housing 20, flows through clearance 26 between the rotor 1 and the stator 24, and exits through the end face 30 at the distal end of the motor housing. The purging pressure is chosen such that it is higher than the blood pressure present, in order to thereby prevent blood from penetrating into the motor housing. Depending on the case of application, the pressure of the purge fluid is between 300 and 1400 mmHg at the motor where the pressure is built up.

Well suited as a purge fluid is a fluid having a viscosity higher than the viscosity of water ($\eta$=0.75 mPa·s at 37° C.), in particular a purge fluid having a viscosity at 37° C. of 1.2 mPa·s or higher. For example, a solution of 5% to 40% glucose in water for injection can be used, but physiological saline solution is also suitable.

Upon rotation of the impeller 34, blood (schematically illustrated by unfilled arrows) is sucked through the end face suction opening 37 of the pump housing 32 and conveyed backward within the pump housing 32 in the axial direction. Through outlet openings 38 of the pump housing 32, the blood flows out of the pump section 12 and further along the motor housing 20. It is also possible to operate the pump section with the reverse conveying direction, with the blood being sucked in along the motor housing 20 and exiting from the opening 37.

The motor shaft 25 is mounted in radial bearings 27 and 31 at the proximal end of the motor housing, on the one hand, and at the distal end of the motor housing, on the other hand. Furthermore, the motor shaft 25 is also mounted axially in an axial bearing 39. Should the blood pump be used for conveying blood also or only in the reverse direction, a corresponding axial bearing 39 is also/only provided at the proximal end of the motor housing 20 in a corresponding manner.

It is stressed that the blood pump described above is just an example, the present invention also being applicable to different blood pumps comprising an electric motor, i.e. requiring permanent magnets.

Intravascular blood pumps must meet numerous requirements. Due to their placement within a living body they should be as small as possible. The smallest pumps presently in use have an outer diameter of about 4 mm. Nevertheless, the pumps must convey high-volume flows in human blood circulation. Therefore, the minute pumps have to be high-performance engines.

Furthermore, the implantable blood pumps must not detrimentally influence their biological environment such as the blood to be pumped and the surrounding tissue.

Therefore, the pumps should be biocompatible in a broad sense, i.e. they should not contain or produce any potentially noxious materials or considerable heat that might damage the body or constituents thereof.

In addition, replacement of a pump is burdensome to the patient. It follows from this, and of course also from financial considerations, that intravascular blood pumps should have a long useful life.

Materials and design of the intravascular blood pumps must be appropriately selected and specifically adapted to meet these various requirements.

Importantly, an appropriate permanent magnet for the electric motor must be selected. With regard to efficiency and longevity of the pump, the magnet should have a strong magnetic field, i.e. high remanence, high resistance to demagnetization. i.e. high coercivity, and a high saturation magnetization. In this respect, rare-earth permanent magnets, in particular those having neodymium as the rare-earth metal, and especially neodymium iron boron (NdFeB) permanent magnets, are the magnets of choice. Other rare-earth iron boron permanent magnets may also be used.

The stronger the magnet, the smaller the magnet can be while still generating sufficient rotational force. Thus, the stronger the magnet, the smaller the electric motor can be. NdFeB permanent magnets are the strongest permanent magnets currently available. They seem to be ideal for use in intravascular blood pumps.

It is well-known that the magnetic properties of rare-earth metal based magnets, for example of NdFeB magnets, depend on the particular alloy composition, microstructure, and the manufacturing techniques employed. NdFeB magnets are available as polymer-bonded magnets and as sintered magnets. Sintered magnets are superior in magnetic properties. They are prepared by alloying the raw materials, grinding to powder, pressing and sintering. During or after preparation, an external magnetic field is applied in order to magnetize the material. A well-studied magnet is a fine-crystalline sintered material wherein $Nd_2Fe_{14}B$ crystals are surrounded by a thin layer particularly rich in neodymium.

While neodymium iron boron magnets have magnetic properties rendering them particularly suitable for use in electric motors of intravascular blood pumps, they also have a serious disadvantage. Namely, commercially available NdFeB magnets, which consist mainly of neodymium, iron and boron, and in particular the sintered neodymium iron boron magnets which have a very active neodymium-rich phase at the grain boundaries, are very vulnerable to corrosion. The magnets may be, for example, corroded by oxygen and moisture in air, in particular, but not only, at the grain boundaries. The corrosion leads to a profound decrease in the magnetic properties, and if the corrosion progresses while the magnet is in use, the performance of the blood pump using the magnet deteriorates. The phenomenon is exacerbated by the tendency of neodymium iron boron magnets to act as a sponge for corrosion products, breaking the structure and leading to spalling off of pieces from the surface of the magnet and finally to crumbling of the magnet.

Unfortunately, liability to corrosion is a property which is common to all rare-earth metals. Therefore, all rare earth metal-based permanent magnets have an unfavorable tendency to corrode, as explained for NdFeB magnets above. For currently available magnets it can be said, as a rule of thumb, that the stronger the magnet, the greater its liability to corrosion.

In an intravascular blood pump, the magnets have to work in a corrosive environment, namely, in the purging liquid flowing between the rotor and the stator (see FIG. 1). As described above, the purge fluid is typically an aqueous fluid, possibly a fluid containing chloride. Chloride is highly corrosive for rare earth metal-based magnets, but also water, and oxygen dissolved in the water, cause severe corrosion within very short time spans of only a few hours.

Clearly, rare earth metal-based permanent magnets, such as neodymium iron boron magnets, for intravascular blood pumps need to be protected against corrosion.

Various measures for protecting neodymium iron boron magnets and other rare earth metal-based magnets against corrosion are known. For example, corrosion resistance may be improved by coating the magnets with protective coatings.

Usual coatings are nickel coatings and coatings based on epoxy resins, and, especially for blood pumps, titanium coatings and Parylene coatings are known. These coatings, however, also have disadvantages. Even if biocompatible metals and organic resins are respectively selected, such as titanium and Parylene, there is the problem that metal coatings must be relatively thick in order to provide sufficient protection. As a result, the gap between the magnet and the windings in the electric motor of the blood pump must be relatively large. A large gap has a strong negative effect on the performance of the electric motor. A large gap demands a higher motor current, and high motor currents produce undesirable heat which may lead to damage of blood and tissue.

Further, organic materials such as Parylene have thermal expansion coefficients which are considerably different from the thermal expansion coefficient of the magnet. Therefore, temperature variations during use of the magnet often lead to cracking and/or delamination of the coating.

EP 3 319 098 A1 discloses a coating for permanent magnets comprising a metal layer, a metal-oxide layer having a thickness of a few nanometers such as e.g. naturally formed upon exposure of an aluminum layer to air, a linker layer, and a layer of poly(2-chloro-p-xylylene). The coating provides good corrosion protection. However, the production process lacks high reproducibility, but rather yields an undesirably high number of magnets being insufficiently protected against corrosion, in particular when coatings are made thin. Further improvement is desirable.

At present, no biocompatible coating for permanent magnets, e.g. neodymium iron boron magnets, is known to fulfil all the requirements for use in an intravascular blood pump in a satisfactory manner. Such a coating must be excellent in corrosion resistance itself, must be thin but nevertheless dense, must not develop cracks or other defects during use, and must reliably and closely adhere to the magnet. Furthermore, the coating process should yield highly reproducible results, i.e. the number of magnets that must be sorted out, should be low. Of course, the coating must be biocompatible, and it must coat with uniform thickness either the complete magnet or at least those portions of the magnet which are exposed to a corrosive environment during use of the magnet. This is particularly demanding because many magnets have a porous surface and a shape comprising edges. Therefore, permanent magnets such as rare earth metal-based magnets, e.g. neodymium iron boron magnets, for use in intravascular blood pumps constitute items which cannot be easily coated with a uniform thickness.

The present invention provides a solution to the problems described above.

The present invention provides permanent magnets having a protective coating thereon which reliably protects the magnets against corrosion while in use in an intravascular blood pump over an extended period of time, and a method for producing the protective coating with high reproducibility. The protective coating is particularly thin, thus allowing to produce very small magnets and, therefore, very small blood pumps.

The subject-matter of the present invention involves a corrosion-resistant permanent magnet having the features disclosed herein, methods for producing corrosion-resistant permanent magnets, the methods having the features disclosed herein and an intravascular blood pump having the features disclosed herein. In particular, the invention provides the following:

1. A corrosion-resistant permanent magnet comprising a magnet body and a composite coating provided on and covering surfaces of the magnet body, the composite coating comprising, in the order recited,
   a first metal oxide layer in physical contact with the magnet body,
   a metal layer,
   a second metal oxide layer,
   a linker layer, and
   a layer formed from poly(2-chloro-p-xylylene).
2. The magnet having the features indicated in (1) above, wherein the magnet body is a sintered magnet body.
3. The magnet having the features indicated in (1) or (2) above, wherein the magnet body is rare earth metal based.
4. The magnet having the features indicated in (3) above, wherein the rare earth metal is neodymium.
5. The magnet having the features indicated in any one of (1) to (4) above, wherein the magnet body is a rare earth metal iron boron permanent magnet.
6. The magnet having the features indicated in (4) or (5) above, wherein the magnet body is a sintered magnet body having $Nd_2Fe_{14}B$ crystals and a neodymium iron boron material surrounding the $Nd_2Fe_{14}B$ crystals, said neodymium iron boron material being richer in neodymium than the $Nd_2Fe_{14}B$ crystals.
7. The magnet having the features indicated in any one of (1) to (6) above, wherein the magnet body is rod-shaped with all edges being rounded.
8. The magnet having the features indicated in any one of (1) to (7) above, wherein the linker forming the linker layer is selected from silanes, mercaptans, phosphines, disulfides, and silanes having a thiol, phosphine or disulfide group.
9. The magnet having the features indicated in (8) above, wherein the silanes are selected from alkoxysilanes or alkoxysilanes having an acryloyloxy or methacryloyloxy functional group, or linkers having bis-trimethoxysilyl or bis-triethoxysilyl functional groups.
10. The magnet having the features indicated in (9) above, wherein the silane is 3-(trimethoxysilyl)propyl methacrylate.
11. The magnet having the features indicated in (8) above, wherein the silanes have a hydride functional group.
12. The magnet having the features indicated in any one of (1) to (11) above, wherein the metal of the metal layer is selected from aluminum, titanium, tantalum, niobium, zirconium, iridium, platinum, gold, iron and alloys comprising at least one of aluminum, titanium, tantalum, niobium and zirconium.
13. The magnet having the features indicated in any one of (1) to (12) above, wherein the metal of the metal layer is aluminum or titanium or an alloy of aluminum or titanium.
14. The magnet having the features indicated in any one of (1) to (13) above, wherein the oxide of the first metal oxide layer and/or the second metal oxide layer is an oxide of at least one of aluminum, titanium, tantalum, niobium, zirconium, silicium, iridium and hafnium.
15. The magnet having the features indicated in any one of (1) to (14) above, wherein the oxide of the first metal oxide layer is $Al_2O_3$ or $TiO_2$ or a mixed oxide of $Al_2O_3$ and $TiO_2$.
16. The magnet having the features indicated in any one of (1) to (15) above, wherein the oxide of the second metal oxide layer is $Al_2O_3$ or $TiO_2$ or a mixed oxide of $Al_2O_3$ and $TiO_2$.
17. The magnet having the features indicated in any one of (1) to (16) above, wherein
   the metal layer is in physical contact with the first metal oxide layer,
   the second metal oxide layer is in physical contact with the metal layer,
   the linker layer is in physical contact with the second metal oxide layer, and
   the poly(2-chloro-p-xylylene) layer is in physical contact with the linker layer.
18. The magnet having the features indicated in any one of (1) to (16) above, comprising a further metal layer and, optionally, a further metal oxide layer between the second metal oxide layer and the linker layer, wherein
   the metal layer is in physical contact with the first metal oxide layer,
   the second metal oxide layer is in physical contact with the metal layer,
   the further metal layer is in physical contact with the second metal oxide layer,
   the further metal oxide layer, if present, is in physical contact with the further metal layer,
   the linker layer is in physical contact with the further metal layer or, if present, the further metal oxide layer, and
   the poly(2-chloro-p-xylylene) layer is in physical contact with the linker layer.
19. The magnet having the features indicated in (18) above, wherein the metal of the further metal layer is selected from aluminum, titanium, tantalum, niobium, zirconium, iridium, platinum, gold, iron and alloys comprising at least one of aluminium, titanium, tantalum, niobium and zirconium.
20. The magnet having the features indicated in (18) or (19) above, wherein the metal of the further metal layer is aluminum.
21. The magnet having the features indicated in any one of (18) to (20) above, comprising the further metal oxide layer, wherein the oxide of the further metal oxide layer is an oxide of at least one of aluminum, titanium, tantalum, niobium, zirconium, silicium, iridium and hafnium.
22. The magnet having the features indicated in (21) above, wherein the oxide of the further metal oxide layer is $Al_2O_3$.
23. The magnet having the features indicated in any one of (18) to (22) above, wherein the linker is a linker as indicated in any one of (8) to (11) above.
24. The magnet having the features indicated in any one of (18) to (23) above, wherein the linker is selected from mercaptans, phosphines, disulfides, and silanes having a thiol, phosphine or disulfide group.
25. The magnet having the features indicated in (24) above, wherein the linker is selected from 3-(2-pyridylethyl)thiopropyl trimethoxysilane, 3-(4-pyridylethyl) thiopropyl trimethoxysilane, 2-(diphenylphosphino)

ethyl triethoxysilane, bis(2-methacryloyl)oxyethyldisulfide, and dihexadecyldisulfide.

26. The magnet having the features indicated in any one of (1) to (25) above, wherein the thickness of the first metal oxide layer and the second metal oxide layer, which is the same or different, is in a range of from 5 nm to 200 nm, or from 80 nm to 120 nm, or from 50 nm to 100 nm, or wherein the thickness of the first and the second metal oxide layer is about 100 nm each.

27. The magnet having the features indicated in any one of (20) to (26) above, comprising the further metal oxide layer, wherein the thickness of the further metal oxide layer is in the range of from 5 nm to 200 nm, or from 80 nm to 120 nm, or from 50 nm to 100 nm, or is about 100 nm.

28. The magnet having the features indicated in any one of (1) to (25) above, wherein the second metal oxide layer and/or the further metal oxide layer is a native metal oxide layer.

29. The magnet having the features indicated in (28) above, wherein the native metal oxide layer has a thickness in the range of from 1 nm to 5 nm.

30. The magnet having the features indicated in any one of (1) to (29) above, wherein the thickness of the metal layer is in a range from 0.1 to 10 μm, or from 0.5 to 10 μm, or from 2 to 6 μm, or is about 4 μm.

31. The magnet having the features indicated in any one of (20) to (30) above, wherein the thickness of the further metal layer is up to 29 μm, and is preferably in a range of from 2 μm to 20 μm or from 10 μm to 18 μm, or is about 15 μm.

32. The magnet having the features indicated in any one of (1) to (31) above, wherein the linker layer is a monolayer, or wherein the thickness of the linker layer is in a range of from 20 nm to 150 nm, or from 50 nm to 100 nm.

33. The magnet having the features indicated in any one of (1) to (32) above, wherein the thickness of the layer formed from poly(2-chloro-p-xylylene) is in a range of from 3 μm to 20 μm, or from 10 μm to 17 μm, or is about 15 μm.

34. The magnet having the features indicated in any one of (1) to (33) above, wherein the thickness of the composite coating is no more than 50 μm.

35. The magnet having the features indicated in any one of (1) to (19) above, wherein the metal layer is omitted, and the composite coating further comprises, in the order recited, on the layer formed from poly(2-chloro-p-xylylene),
 a third metal oxide layer,
 a further linker layer, and
 a further layer formed from poly(2-chloro-p-xylylene).

36. The magnet having the features indicated in (35) above, comprising an intermediate metal oxide layer between the layer formed from poly(2-chloro-p-xylylene) and the third metal oxide layer.

37. The magnet having the features indicated in (35) above, wherein
 the thickness of the first metal oxide layer, the second metal oxide layer and the third metal oxide layer is in a range of from 5 nm to 300 nm, each.

38. The magnet having the features indicated in (36) above, wherein the thickness of the first metal oxide layer, the second metal oxide layer, the intermediate metal oxide layer, and the third metal oxide layer is in a range of from 5 nm to 200 nm, each.

39. The magnet having the features indicated in any one of (35) to (38) above, wherein the thickness of the linker layer and the thickness of the further linker layer is the same or different, and is in a range of from 20 nm to 150 nm, or from 50 nm to 100 nm, or is essentially a monolayer thickness.

40. The magnet having the features indicated in any one of (35) to (39) above, wherein the thickness of the layer formed from poly(2-chloro-p-xylylene) is in a range of from 0.5 μm to 4 μm, or from 1 μm to 2 μm, and/or the thickness of the further layer formed from poly(2-chloro-p-xylylene) is in a range of from 3 μm to 20 μm, or from 10 μm to 15 μm, or is about 3 μm.

41. The magnet having the features indicated in any one of (35) to (40) above, wherein the thickness of the composite coating is no more than 50 μm.

42. The magnet having the features indicated in any one of (35) to (41) above, wherein the oxide of the first metal oxide layer is $Al_2O_3$ and the oxide of the second metal oxide layer is $TiO_2$, or the oxide of the first metal oxide layer is $TiO_2$ and the oxide of the second metal oxide layer is $Al_2O_3$, or the oxides of the first and second metal oxide layers are $Al_2O_3$, or the oxides of the first and second metal oxide layers are $TiO_2$.

43. The magnet having the features indicated in any one of (35) to (42) above, wherein the oxide of the third metal oxide layer is $TiO_2$ or $Al_2O_3$, preferably $TiO_2$.

44. The magnet having the features indicated in any one of (36) to (43) above, wherein the oxide of the intermediate metal oxide layer is $Al_2O_3$ or $TiO_2$, preferably $Al_2O_3$, and is different from the oxide of the third metal oxide layer.

45. A method for producing a corrosion-resistant permanent magnet, the method comprising
 providing a non-magnetized magnet body,
 forming a first metal oxide layer on surfaces of the magnet body,
 forming a metal layer on the first metal oxide layer,
 forming a second metal oxide layer on the metal layer,
 optionally, forming at least one further layer on the second metal oxide layer,
 forming a linker layer on the second metal oxide layer or, if present, on the at least one further layer,
 forming a layer of poly(2-chloro-p-xylylene) on the linker layer, and
 magnetizing the magnet body.

46. The method having the features indicated in (45) above, the method comprising forming the at least one further layer, wherein the at least one further layer is a further metal layer.

47. The method having the features indicated in (46) above, the method further comprising forming a further metal oxide layer on the further metal layer.

48. The method having the features indicated in any one of (45) to (47) above, wherein the oxide of the first metal oxide layer and/or the oxide of the second metal oxide layer is an oxide as indicated in any one of (14) to (16) above.

49. The method having the features indicated in any one of (45) to (48) above, wherein the metal of the metal layer is a metal as indicated in (12) or (13) above.

50. The method having the features indicated in any one of (46) to (49) above, wherein the metal of the further metal layer is a metal as indicated in (21) or (22) above.

51. The method having the features indicated in any one of (47) to (50) above, wherein the oxide of the further metal oxide layer is an oxide as indicated in (23) or (24) above.
52. The method having the features indicated in any one of (45) to (51) above, wherein the linker of the linker layer is a linker as indicated in any one of (8) to (11), (17) and (18) above.
53. The method having the features indicated in any one of (45) to (52) above, wherein the first metal oxide layer and/or the second metal oxide layer are formed by a process selected from physical vapor deposition, chemical vapor deposition, sputtering, a sol-gel process and flame spraying, or by oxidizing a corresponding metal layer.
54. The method having the features indicated in (53) above, wherein the physical vapor deposition process is a process using plasma or is a process without using plasma or is an ion vapor deposition process.
55. The method having the features indicated in (53) above, wherein the first metal oxide layer and/or the second metal oxide layer are formed by an atomic layer deposition process, the atomic layer deposition process being a process using plasma or a process without using plasma.
56. The method having the features indicated in any one of (45) to (55) above, wherein the metal layer is formed by a process selected from physical vapor deposition, chemical vapor deposition, sputtering, and atomic layer deposition.
57. The method having the features indicated in (56) above, wherein the metal layer is formed by a physical vapor deposition process using plasma or a physical vapor deposition process without using plasma or by an ion vapor deposition process.
58. The method having the features indicated in any one of (46) to (57) above, wherein the further metal layer is formed by a plating process, a sputtering process, a physical vapor deposition process, or an atomic layer deposition process.
59. The method having the features indicated in (58) above, wherein the plating process is a galvanic deposition process from an ionic liquid.
60. The method having the features indicated in any one of (47) to (59) above, wherein the further metal oxide layer is formed by a process as indicated in any one of (53) to (55) above.
61. The method having the features indicated in any one of (45) to (60) above, wherein the linker layer is formed by applying a linker by physical vapor deposition using plasma, or by physical vapor deposition without using plasma, or by a wet process, or by a plasma deposition process, or by a combination thereof.
62. The method having the features indicated in any one of (45) to (61) above, wherein the layer of poly(2-chloro-p-xylylene) is formed by a plasma deposition process of dichloro[2.2]paracyclophane.
63. The method having the features indicated in any one of (45) to (62) above, wherein the layers have thicknesses as indicated in any one of (26) to (34) above.
64. The method having the features indicated in any one of (45) to (63) above, wherein the magnet body is a magnet body as indicated in any one of (1) to (7) above.
65. A method for producing a corrosion-resistant permanent magnet, the method comprising
   providing a non-magnetised magnet body,
   forming a first metal oxide layer on surfaces of the magnet body,
   forming a second metal oxide layer on the first metal oxide layer,
   forming a linker layer on the second metal oxide layer,
   forming a layer of poly(2-chloro-p-xylylene) on the linker layer,
   optionally, forming an intermediate metal oxide layer on the poly(2-chloro-p-xylylene) layer,
   forming a third metal oxide layer on the poly(2-chloro-p-xylylene) layer or, if present, on the intermediate metal oxide layer,
   forming a further linker layer on the third metal oxide layer,
   forming a further layer of poly(2-chloro-p-xylylene) on the further linker layer, and
   magnetizing the magnet body.
66. The method having the features indicated in (65) above, wherein the oxide of the first metal oxide layer is $Al_2O_3$, and the oxide of the second metal oxide layer is $TiO_2$, or the oxide of the first metal oxide layer is $TiO_2$ and the oxide of the second metal oxide layer is $Al_2O_3$, or the oxides of the first and second metal oxide layers are both $Al_2O_3$ or are both $TiO_2$.
67. The method having the features indicated in (65) or (66) above, wherein the oxide of the third metal oxide layer is $TiO_2$ or $Al_2O_3$, preferably $TiO_2$.
68. The method having the features indicated in any one of (65) to (67) above, comprising forming the intermediate metal oxide layer, wherein the oxide of the intermediate metal oxide layer is $Al_2O_3$ or $TiO_2$, preferably $Al_2O_3$, and is different from the oxide of the third metal oxide layer.
69. The method having the features indicated in any one of (65) to (68) above, wherein the linker of the linker layer and/or the further linker layer is a linker as indicated in any one of (8) to (11) above.
70. The method having the features indicated in any one of (65) to (69) above, wherein the first metal oxide layer and/or the second metal oxide layer are formed by a process selected from physical vapor deposition, chemical vapor deposition, sputtering, a sol-gel process, flame spraying, and atomic layer deposition.
71. The method having the features indicated in any one of (65) to (70) above, wherein the third metal oxide layer and/or, if present, the intermediate metal oxide layer are formed by an atomic layer deposition process or by a physical vapor deposition process.
72. The method having the features indicated in any one of (65) to (71) above, wherein the linker layer and/or the further linker layer is formed by applying a linker by physical vapor deposition using plasma, or by physical vapor deposition without using plasma, or by a wet process, or by a plasma deposition process, or by a combination thereof.
73. The method having the features indicated in any one of (65) to (72) above, wherein the layer of poly(2-chloro-p-xylylene) is formed by a plasma deposition process of dichloro[2.2]paracyclophane.
74. The method having the features indicated in any one of (65) to (73) above, wherein the layers have thicknesses as indicated in any one of (37) to (41) above.
75. The method having the features indicated in any one of (65 to 74) above, wherein the magnet body is a magnet body as indicated in any one of (1) to (7) above.

76. An intravascular blood pump comprising an electric motor, wherein the electric motor comprises a permanent magnet as indicated in any one of (1) to (44) above.

A magnet is corrosion resistant in the sense of this invention if it passes the following test:

The coated magnet is subjected to corrosion testing in an aqueous solution containing 0.9 weight % sodium chloride at 60° C. (accelerated corrosion test). Corrosion of the magnetic material results in lifting or deformation of the coating. Thus, lifting of the coating or formation of a bulge at a surface of a test specimen indicates corrosion of the magnetic material. Formation of a bulge having a height of 0.1 mm as well as lifting of the coating is defined as being indicative of magnet failure. Magnets pass the test when time until failure is at least 30 days.

According to the present invention, a strong permanent magnet comprises a coating either completely surrounding a magnet body or covering at least those surfaces of the magnet body which are exposed to fluid when the magnet is operating in an intravascular blood pump. The coating renders the magnet resistant to corrosion while in use in an intravascular blood pump. Preferred magnet bodies are sintered magnets consisting primarily of neodymium, iron, and boron, with fine tetragonal magnetic $Nd_2Fe_{14}B$ crystals and a neodymium rich non-magnetic phase surrounding the crystals, as described above. Typically, the $Nd_2Fe_{14}B$ crystals forming the main phase have a mean crystal diameter within a range of 1 to 80 μm. The non-magnetic neodymium rich phase makes up from 1% to 50% by volume of the magnet body. These magnets are readily available commercially. They are preferred because they have high magnetic characteristics, and because they are particularly strong, i.e. have a high flux density. For the reasons indicated above, an application in intravascular blood pumps requires particularly strong magnets. In principle, however, the inventive corrosion-resistant coating can be applied to any material requiring protection against corrosion, for example different rare-earth iron boron magnetic materials or any other magnetic materials.

The inventive coating is a composite coating provided on surfaces of the magnet body, i.e. the actual magnetic material. According to a first embodiment, the composite coating comprises a first metal oxide layer on surfaces of the magnet body, a metal layer on the first metal oxide layer at the exposed surfaces thereof, a second metal oxide layer on the metal layer, a layer formed from poly(2-chloro-p-xylylene) and a linker layer between the second metal oxide layer and the poly(2-chloro-p-xylylene) layer. The first metal oxide layer, the metal layer and the second metal oxide layer, together, form an inorganic layer.

According to a second embodiment, a further metal layer is provided between the second metal oxide layer and the linker layer. In this embodiment, the first metal oxide layer, the metal layer, the second metal oxide layer, and the further metal layer, together, form an inorganic layer.

In a preferred variant, a further metal oxide layer is provided on the further metal layer. In this particular embodiment, the first metal oxide layer, the metal layer, the second metal oxide layer, the further metal layer and the further metal oxide layer, together, form an inorganic layer. The further metal oxide layer may be artificially formed or may be a native oxide layer, i.e. an oxide layer which automatically forms upon exposure of the further metal layer to air. This applies also to the second metal oxide layer of the first embodiment and the second embodiment.

According to a third embodiment, the composite coating comprises a first layer structure and a second layer structure. The first layer structure is provided on surfaces of the magnet body, and the second layer structure is provided on the first layer structure. The first layer structure comprises a first metal oxide layer (on surfaces of the magnet body), a second metal oxide layer on the first metal oxide layer, a layer formed from poly(2-chloro-p-xylylene) and a linker layer between the second metal oxide layer and the poly(2-chloro-p-xylylene) layer. The metal oxide layers, together, form an inorganic layer. The second layer structure comprises a third metal oxide layer (on the first layer structure), a layer formed from poly(2-chloro-p-xylylene), and a linker layer between the third metal oxide layer and the poly(2-chloro-p-xylylene). The third metal oxide layer forms an inorganic layer.

An additional (intermediate) metal oxide layer may be provided between the first layer structure and the third metal oxide layer. In this case, the second layer structure comprises the intermediate metal oxide layer (on the first layer structure), the third metal oxide layer on the intermediate metal oxide layer, a layer formed from poly(2-chloro-p-xylylene), and a linker layer between the third metal oxide layer and the poly(2-chloro-p-xylylene) layer. The metal oxide layers, together, form an inorganic layer. In this case, the second layer structure comprises the intermediate metal oxide layer (on the first layer structure), the third metal oxide layer on the intermediate metal oxide layer, a layer formed from poly(2-chloro-p-xylylene), and a linker layer between the third metal oxide layer and the poly(2-chloro-p-xylylene) layer.

The poly(2-chloro-p-xylylene) layer constitutes an organic layer. Therefore, in each embodiment, the composite coating comprises at least one inorganic layer and at least one organic layer.

The metal oxides of the first layer structure and the second layer structure may be the same or different.

Rare earth metal-based magnets as purchased from a supplier are typically protected by a phosphate coating. This phosphate coating may be removed, for example by washing with an acid, prior to application of the composite coating. However, the phosphate coating does not detrimentally interfere with the coating or the coating process according to the present invention and may, therefore, remain on the magnet body. Preferably, the phosphate coating is not removed. Not removing the phosphate coating saves one process step and avoids introducing impurities during such a process step. It is, however, preferable to clean the magnet prior to application of the first metal oxide layer. Cleaning is preferably performed by washing the magnet with an organic solvent, for example an alcohol. Particularly preferred cleaning agents are isopropanol and a mixture of isopropanol and ethanol. After washing with an organic solvent, the magnet is dried, for example in vacuum or in an air stream.

After cleaning and drying, the first metal oxide layer is applied to the surface of the magnet body. It is essential to the present invention that a metal oxide layer is provided directly on the surfaces of the magnet, i.e. is in physical contact with the magnet (contact with a phosphate coated magnet is regarded as a direct contact with the magnet). Metal oxides adhere well to the relatively rough magnet surfaces and, therefore, are not easily detached therefrom even under the harsh operating conditions in an intravascular blood pump. As a consequence, corrosion resistance of the magnet is significantly improved, and an intravascular blood pump comprising the magnet works failure-free over a prolonged period of time. Furthermore, it is advisable to apply the inventive composite coatings to the non-magnetized magnet bodies, and to magnetize the magnet bodies only after the coatings have been applied. Magnetizing a magnet body before coating application is not appropriate.

In the first and second embodiments, the metal oxides forming the first metal oxide layer and the second metal oxide layer may be the same or different. Preferably, the oxide of the first metal oxide layer and/or the second metal oxide layer is an oxide of at least one of aluminum, titanium, tantalum, niobium, zirconium, silicium, iridium and hafnium. Particularly preferred oxides for the first metal oxide layer and/or the second metal oxide layer are $Al_2O_3$, $TiO_2$ and mixtures thereof. The same applies to the further metal oxide layer which is optionally present in the second embodiment.

In the third embodiment, the composition of the first metal oxide layer is typically different from the composition of the second metal oxide layer, and the composition of the third metal oxide layer is typically different from the composition of the intermediate metal oxide layer, if present, and the oxides of the first inorganic layer may be the same or different from the metal oxide(s) of the second inorganic layer. Metal oxides suitable for forming the first metal oxide layer, the second metal oxide layer, the third metal oxide layer and the intermediate metal oxide layer are the same as in the case of the first embodiment and the second embodiment. Preferably, the oxide of the first metal oxide layer is $Al_2O_3$ and the oxide of the second metal oxide layer is $TiO_2$ or the oxide of the first metal oxide layer is $TiO_2$ and the oxide of the second metal oxide layer is $Al_2O_3$. The oxide of the third metal oxide layer is preferably $TiO_2$ or $Al_2O_3$, and $TiO_2$ is particularly preferred. If an intermediate metal oxide layer is present, the oxide of the intermediate metal oxide layer is preferably $Al_2O_3$ or $TiO_2$, and $Al_2O_3$ is particularly preferred.

The oxides of the first metal oxide layer and the second metal oxide layer may also be identical. In this case, the first metal oxide layer and the second metal oxide layer are applied by the same or by different processes. This applies analogously to the third metal oxide layer and the intermediate metal oxide layer.

In the first embodiment and the second embodiment, a metal layer is provided between the first metal oxide layer and the second metal oxide layer. Exemplary metals for forming the metal layer are aluminum, titanium, tantalum, niobium, zirconium, iron, iridium, platinum, gold, and alloys comprising at least one of aluminum, titanium, tantalum, niobium and zirconium. Particularly preferred metals are aluminum and titanium. Specifically in the second embodiment iron is also preferred.

In the second embodiment, a further metal layer is provided on the second metal oxide layer. Exemplary metals for forming the further metal layer are the same as in the case of the metal layer, with aluminum being the preferred metal.

In all embodiments, methods for forming the metal oxide layers are not particularly limited, but atomic layer deposition (ALD) is preferred. In particular, the third metal oxide layer and, if present, the intermediate metal oxide layer of the third embodiment are preferably formed by an ALD process.

ALD is a thin-film deposition method in which a film is grown on a substrate by exposing the substrate surface to alternate gaseous substances, so-called precursors. The precursors are introduced into a reactor containing the substrate to be coated in a series of sequential, non-overlapping pulses, i.e. the precursors are never present simultaneously in the reactor.

In each pulse, the precursor which has been introduced into the reactor is adsorbed on the surface of the substrate to be coated until all available reactive sites on the surface are consumed. Then, any excess precursor is removed from the reactor. Thereafter, a second precursor, different from the first precursor, is introduced into the reactor and adsorbed on the substrate surface, undergoing a chemical reaction with the previously adsorbed first precursor. Then again, any excess precursor and gaseous reaction products are removed from the reactor. Depending on the type of layer to be deposited, further precursors, different from the first and second precursors, may be introduced into the reactor, adsorbed and reacted, and any excess precursors and reaction products removed from the reactor.

A single exposure to all of the precursors is called an ALD cycle.

Ideally, each ALD cycle produces a monolayer of coating material. Therefore. ALD allows controlling layer thickness and composition at an atomic level. It can coat large substrates having complex shapes with uniform and conformal coatings without defects which might constitute a site rendering the composite coating more susceptible to attacks by corrosive agents.

In the case of forming an aluminum oxide layer, preferred precursor materials for performing the ALD process are $AlX_3$ and water (in gaseous form). In $AlX_3$, X represents lower alkyl groups (which may be the same or different), or lower alkyl groups (which may be the same or different) and hydrogen, or halogen atoms (which may be the same or different). Particularly preferred $AlX_3$ compounds are trimethyl aluminum (TMA), triethyl aluminum (TEA), triisobutyl aluminum (TIBA), dimethyl aluminum (DMAlH), and aluminum trichloride ($AlCl_3$).

In an exemplary ALD process for producing an aluminum oxide layer, the magnet is placed in a reaction chamber, and $AlX_3$ in a suitable inert carrier gas, for example argon, and at an appropriate temperature, for example about 300° C., is introduced into the reaction chamber. The $AlX_3$ adsorbs on the surface of the magnet or a coating already formed on the magnet almost instantaneously, and any excess $AlX_3$ and carrier gas is removed by evacuating, for example to about 0.1 to 0.01 Pa. Thereafter, humid air is introduced. The water contained therein adsorbs on the surface and reacts with $AlX_3$, forming aluminum oxide on the surface as well as HX. The air and any excess $AlX_3$ as well as HX is removed by evacuating the reaction chamber again to about 0.1 to 0.01 Pa.

The complete ALD cycle takes from about 10 to 12 seconds and produces an aluminum oxide coating layer thickness of about 0.1 nm. Thus, producing an aluminum oxide layer thickness of about 100 nm requires an ALD process time of about three hours.

ALD is also a preferred method for forming titanium oxide ($TiO_2$), however, ALD is not available for each metal oxide, because appropriate precursors do not exist for each metal oxide.

Other methods which are well suitable for forming the various metal oxide layers of the embodiments of the present invention are, for example, physical vapor deposition, chemical vapor deposition, sputtering, a sol-gel process, flame spraying or oxidizing a previously applied metal layer. In the case of oxidizing a metal layer, the metal of the metal oxide is, of course, identical to the metal of the underlying metal layer, while otherwise the metal of a metal oxide layer and the metal of the underlying metal layer may be different.

Physical vapor deposition may be a process using plasma or without using plasma, or an ion vapor deposition process. Likewise, ALD may be performed with or without using plasma.

As a method particularly suitable for applying niobium oxide, a sol-gel process may be mentioned, and as a method particularly suitable for applying tantalum oxide, applying tantalum metal by physical vapor deposition, followed by oxidation in plasma or in an oven, may be mentioned. When using zirconium oxide, stabilizing with e.g. yttriumoxide is advisable.

Methods such as physical vapor deposition and sputtering may be performed with or without biasing. Biasing is advantageous insofar as it enhances formation of uniform coatings even on surfaces having irregular geometries.

In the first embodiment and the second embodiment, the thickness of the first metal oxide layer, the second metal oxide layer and the further metal oxide layer (if present), which is the same of different, may be in a range of from 5 nm to 200 nm, preferably from 80 nm to 120 nm, more preferably from 50 nm to 100 nm, and most preferably is about 100 nm. The second metal oxide layer and the further metal oxide layer can be native oxide layers, i.e. they can be naturally formed upon exposure of the underlying metal layer to air, if the underlying metal layer allows formation of a native oxide. Native oxide layers preferably have a thickness in the range of 1 nm to 5 nm.

In the third embodiment, the combined thicknesses of the first metal oxide layer, the second metal oxide layer, the third metal oxide layer and, if present, the intermediate metal oxide layer are preferably in the range from 20 nm to 800 nm. Thus, in the case of four metal oxide layers the thickness of each metal oxide layer is preferably in the range of from 5 nm to 200 nm, and in the case of only three metal oxide layers the thickness of each metal oxide layer is preferably in a range of from 5 nm to 300 nm.

In the first embodiment and the second embodiment, methods for forming the metal layer and the further metal layer, respectively, are a dry deposition method in the case of the metal layer, and a wet deposition method or a dry deposition method in the case of the further metal layer.

Exemplary dry methods are chemical vapor deposition, physical vapor deposition (PVD) and ion vapor deposition (IVD), sputtering, and methods such as plasma coating and atomic layer deposition (ALD). IVD yields metal layers having column like structures. Peening is advisable before depositing further layers thereon. Such metal layers also do not have the desired quality. PVD, and in particular Arc-PVD, is the preferred method for producing the metal layers of the composite coatings of the present invention. PVD can produce metal layers having the desired quality and thickness within a reasonable time and at a reasonable cost. In particular, PVD produces homogeneous metal layers. Therefore, the composite coating of the first embodiment and the second embodiment according to this invention comprises a metal layer which has been deposited preferably by PVD, most preferably Arc-PVD. Preferred metals for forming the metal layer are aluminum and/or titanium.

Exemplary reaction conditions for the PVD process are a temperature in the range from about 200° C. to 260° C., and an inert gas atmosphere, for example an argon gas atmosphere.

Exemplary metal layers have a thickness from 0.1 μm to 10 μm, or from 0.5 μm to 10 μm. From the viewpoint of providing optimum corrosion protection, the metal layer is desirably thick, however, the thicker the layer, the more time is required for its application (rendering the process expensive) and, as described above, thick coatings are disadvantageous in that they increase the distance between the magnet body and the windings in the electric motor of the blood pump. Therefore, a preferred thickness is 10 μm or below. On the other hand, from the viewpoint of corrosion protection, the metal layer should have a thickness of at least 0.5 μm, although in some cases also a lower layer thickness may be satisfactory. A more preferred thickness of the metal layer is from 2 μm to 6 μm, and a particularly preferred thickness if about 4 μm.

According to the second embodiment, the composite coating comprises a further metal layer. The further metal layer is applied by the same as or a different method than the metal layer, preferable by a different method. The reason is that while dry methods such as physical vapor deposition yield coatings having good long term stability with a high degree of reproducibility, it appears that wet methods such as galvanic deposition (ion plating) yield metal layers having an enhanced density, i.e. a better quality. Therefore, the second embodiment of this invention combines a metal layer formed preferably by a physical vapor deposition process and a further metal layer formed preferably by a plating process. There are, however, cases wherein wet deposition is not feasible. Gold, for example, is preferably applied by sputtering. The further metal layer, preferably, has a thickness in a range of from 2 μm to 20 μm, more preferably from 10 μm to 18 μm, and most preferably about 15 μm. A plating layer may have a thickness of up to 29 μm.

The preferred metal for forming the further metal layer is aluminum. Galvanic deposition of aluminum is performed out of ionic liquids in a manner usual in the art, for example by using a mixture of aluminum chloride and 1-ethyl-3-methylimidazolium-chloride. The aluminum is preferably pure, e.g. at least 99% pure, and particularly preferably at least 99.9% pure.

In order to enhance the corrosion protection provided by the metal layer/metal oxide layer(s), the metal layer/metal oxide layer(s) is combined with a poly(p-xylylene) polymer layer, in all embodiments of this invention. Poly(p-xylylene) polymers are known under the trade name Parylene. Parylenes may react with hydroxyl group containing surfaces, and are known to form pin-hole free coatings at low layer thicknesses. In addition, they have low dielectric constants (about 3), which is advantageous in implantable blood pumps. A composite coating comprising metal oxide layer(s) and/or metal/metal oxide layer(s) such as the coating according to the present invention, and a Parylene layer is biocompatible and also provides corrosion protection. However, the adhesion of the Parylene layer to a metal layer or a metal oxide layer is not sufficiently strong under the working conditions in an intravascular blood pump. The Parylene layer starts to delaminate after an unacceptably short time, thus exposing the metal or metal oxide layer. The metal layer(s) and/or the metal oxide layer(s) cannot sufficiently protect the magnetic body, and thus corrosion of the magnetic body sets in.

This scenario is prevented by a combination of two measures: provision of an interface layer linking the metal layer or the metal oxide layer and the Parylene layer, and use of a particular Parylene compound.

The compound forming the interface layer, i.e. the linker compound, must be bifunctional. Bifunctional means that the linker compound must have two types of functional groups or molecular moieties of different functionality (reactivity), one functional group or molecular moiety bonding to the metal layer or the metal oxide layer, e.g. by reacting with surface hydroxyl groups of the metal or metal oxide layer, and the other functional group or molecular moiety bonding to Parylene, thus firmly linking the inorganic metal layer or metal oxide layer and the organic Parylene layer. Linking may be provided by covalent bonds or other bonds, e.g. by van der Waals forces.

Linkers having functional groups or moieties bonding to metals or metal oxides, and functional groups or moieties bonding to Parylene, are known. As exemplary linkers, mention may be made of silane compounds, mercaptans, phosphines, disulfides, and silanes having a thiol, phosphine or disulfide group. Depending on the metal, different linker compounds are preferred.

In the case of aluminum, titanium, tantalum, niobium, zirconium, iridium, silicium, hafnium, and oxides of these metals, linkers for the metal layers and for the metal oxide layers are preferably alkoxysilanes, such as methoxysilanes and ethoxysilanes, for example silanes having the formula $(H_3CO)_3Si—R$, with R being e.g. methacrylate, alkylamine, phenylamine, or epoxyalkyl. For bonding to Parylene, the linkers preferably have an acryloyloxy or methacryloyloxy functional group. The carbon chain length between the silyl portion and the (meth)acryloyloxy portion of the linker typically has from 1 to 16 carbon atoms (methyl, ethyl, propyl, butyl, pentyl . . . ). The hydrocarbon chain is typically saturated, but may also contain one or more unsaturated bonds. A particularly preferred linker is 3-(trimethoxysilyl)propyl methacrylate (A-174) from Silquest, but other silane compounds such as G-170 from Silquest (a vinyl-functional silane coupling agent) are also suitable. In addition, linkers having bis-trimethoxysilyl or bis-triethoxysilyl functionalities may be used, for example bis(trimethoxysilylethyl)benzene.

In particular for titanium, zirconium and platinum, linkers having hybrid-functional groups such as trihydrosilanes work well. 10-undecenylsilane and n-octadecylsilane may be specifically mentioned. The silanes are preferably applied at room temperature from the vapor phase or from an aprotic solution. In addition, the above-mentioned alkoxysilanes having (meth)acryloyloxy groups, and the compounds having bis-trimethoxysilyl or bis-triethoxysilyl functionalities, are also suitable.

Linkers suitable for linking the Parylene layer to a gold layer are typically mercaptans, phosphines or disulfides, preferably with longer hydrocarbon chains, such as alkyl- or dialkyl-disulfides with alkyl groups having from 10 to 16 carbon atoms. Such alkyl groups form dense and well ordered layers on the metal or metal oxide surface. However, alkyl groups having only from 1 to 9 carbon atoms may also be used.

Equally appropriate for gold layers are silane linker compounds having thiol, phosphine or disulfide groups. Particularly preferred examples are 3-(2-pyridylethyl)thiopropyl trimethoxysilane, 3-(4-pyridylethyl)thiopropyl trimethoxysilane, 2-(diphenylphosphino) ethyl triethoxysilane, bis(2-methacryloyl)oxyethyldisulfide, and dihexadecyldisulfide.

The bifunctional linkers are preferably applied to the metal or metal oxide surface by a plasma coating process or by physical vapor deposition without plasma or by applying an aprotic, or an alcoholic or an aqueous solution of the bifunctional linker compound to the metal surface or the metal oxide surface. Dry coating of silane compounds in a plasma chamber yields glassy layers comprising Si—O—Si—O— chains arranged substantially parallel to the metal oxide surface and bonded to the surface via oxygen atoms. An organic residue faces away from the surface and is available for bonding to the Parylene. Physical vapor deposition and wet application form interface layers having a similar structure, but without a glassy appearance.

Plasma deposition yields a dense layer with acceptable adherence to Parylene. Physical vapor deposition without plasma yields less dense layers having better adherence to Parylenes than plasma deposited layers. Wet application yields very dense monolayers having an irregular network and a high degree of crosslinking and a high percentage of silicon-bonded oxygen. These layers also adhere very well to Parylene layers. Therefore, wet application is particularly preferable.

Alternatively, plasma application and physical vapor deposition (without plasma) or wet application processes can be combined, i.e. a glassy interface layer is first formed by plasma deposition, followed by physical vapor deposition or wet application of a second linker layer, thus forming a composite linker layer. In such composite linker layer, silicon atoms of the glassy layer are linked covalently to oxygen atoms of the second layer, with organic residues (such as methacrylate, alkylamine, or epoxyalkyl) of the second layer being available for bonding the Parylenes, either covalently or in a different manner, e.g. by van der Waals forces.

The interface layer typically has a thickness in the range from 20 to 150 nm, preferably from 50 to 100 nm. Alternatively, only a monolayer may be applied. Monolayers are obtainable via application of a solution of the linker compound, and evaporation of the solvent.

A Parylene layer, i.e. a poly(p-xylylene)polymer layer, is formed on the interface layer or, in the case of the third embodiment, on the interface layers of both the first and the second layer structure. Poly(p-xylylene)polymers have the structural formula

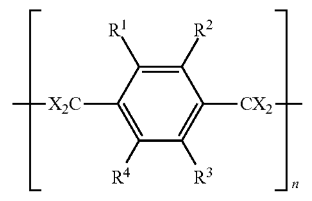

wherein n is the polymerization degree.

Precursors of poly(p-xylylene) compounds are [2.2]paracyclophanes having the structural formula

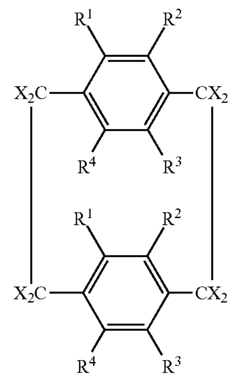

The dimeric compounds are available on the market, for example precursors of Parylene N, Parylene C, Parylene D, and Parylene F. In Parylene N, all of X and R1 to R4 are hydrogen, in Parylene C, one of R1 to R4 is chlorine while the other residues R as well as X are hydrogen, in Parylene D, two of the residues R1 to R4 are chlorine while all other residues are hydrogen, and in Parylene F, the residues X are fluorine while the residues R1 to R4 are hydrogen. Parylene layers are typically used as moisture barriers and dielectric barriers.

At high temperatures (above about 500° C., depending on the particular Parylene) under vacuum, the dimers are cracked to form the corresponding p-xylylene radicals. The monomers polymerize to form poly(p-xylylene) polymers, on the one hand, and bond to the interface layer via the functional groups thereof, e.g. methacrylate groups, on the other hand. Alternatively, they may simply adhere to hydrophobic portions of the interface layer.

It has been found that Parylene C, wherein one of R1 to R4 is chlorine, forms a coating rendering magnetic materials resistant to corrosion under the conditions encountered in intravascular blood pumps, when applied as the cover layer of the composite layer according to the first and the second embodiment, or as the cover layer of the first and the second layer structure according to the third embodiment. The Parylene layer is preferably applied by plasma deposition, and the layer thickness of the uppermost layer is preferably in a range from 3 μm to 20 μm, more preferably from 10 μm to 17 μm, and most preferably about 15 μm. In the third embodiment, the Parylene layer of the first layer structure preferably has a thickness ranging from 0.5 μm to 4 μm, more preferably from 1 μm to 2 μm.

When Parylene C is applied directly onto the surface of the magnetic material, crack formation and delamination of the protective Parylene C layer and corrosion of the magnetic material are observed within a few days. Likewise, if Parylene C is applied onto a metal layer or a metal/metal oxide layer, corrosion of the magnetic material is observed under the conditions in an intravascular blood pump within an unacceptably short time period, due to delamination. In addition, Parylene compounds different from Parylene C do not provide sufficient corrosion protection, even if an adhesion promoter is used, e.g. if applied on a silane based interface layer.

The composite coating of the present invention adheres well to the magnet body, and since it has a structure made up of both inorganic and organic constituents, it provides an effective barrier against both inorganic and organic matter. In addition, glassy interface layers have barrier properties, too.

In a particularly preferred embodiment of the present invention, corrosion protection of the magnetic material is further enhanced by the shape of the magnet body being particularly adapted to allow the formation of a coating covering the magnet body with a uniform thickness. To this aim, the magnet body has no sharp edges, but rather rounded forms such as soft edges. Preferably, the magnet body is rod-shaped having a channel extending therethrough in a longitudinal direction for receiving the motor shaft of an intravascular blood pump, the opposing front faces of the magnet body being bevelled towards the channel. The channel does not need to be coated with the composite coating because in an intravascular blood pump the channel receives the motor shaft and is fixed thereto. Of course, the channel may be coated nevertheless, to be on the safe side.

The magnet body may be a single piece, or may be composed of several segments. In the latter case, each segment is provided with the inventive coating either surrounding it completely or at least the exposed surfaces thereof with a uniform thickness. Preferably, each segment has soft edges.

The present invention will be further explained with reference to the accompanying drawings, wherein FIG. 1 is a schematic longitudinal section of an exemplary embodiment of an intravascular blood pump.

Figure 2:
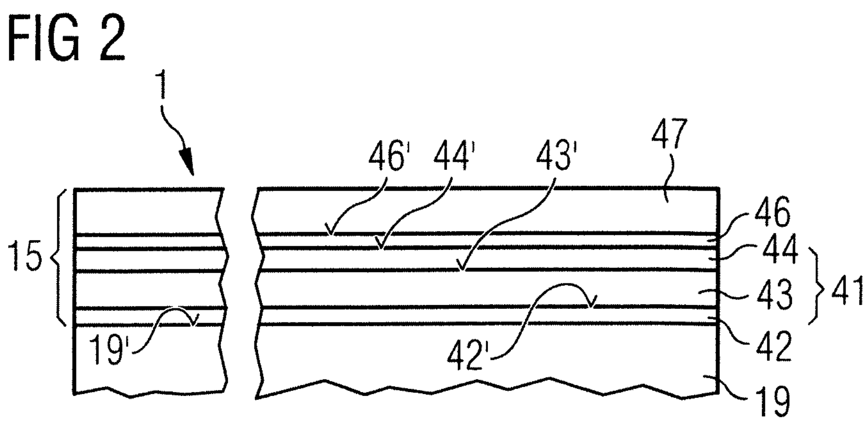
Figure 3:
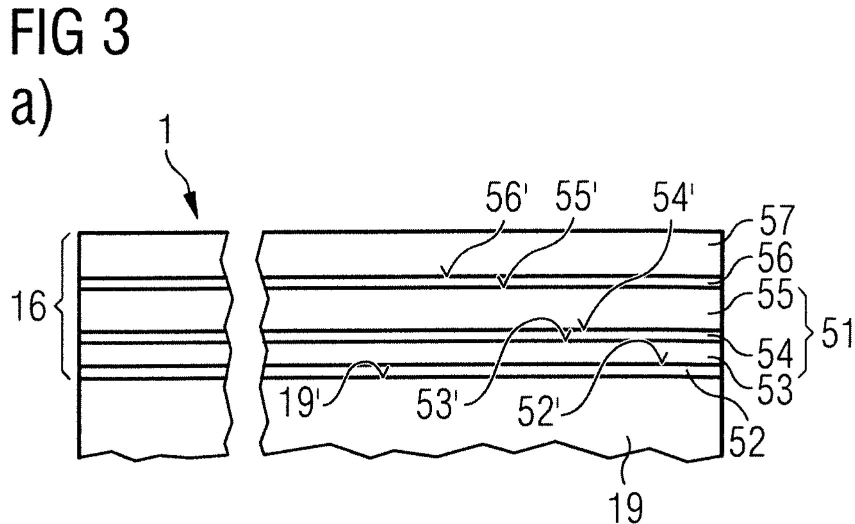
Figure 3:
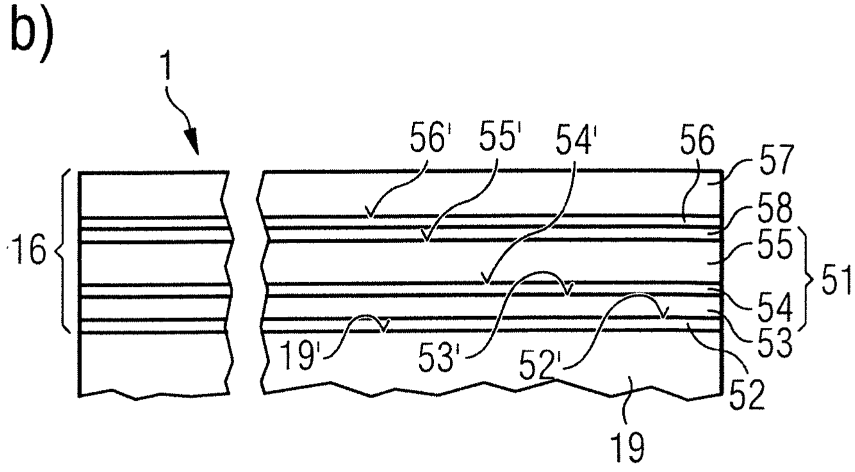
Figure 4:
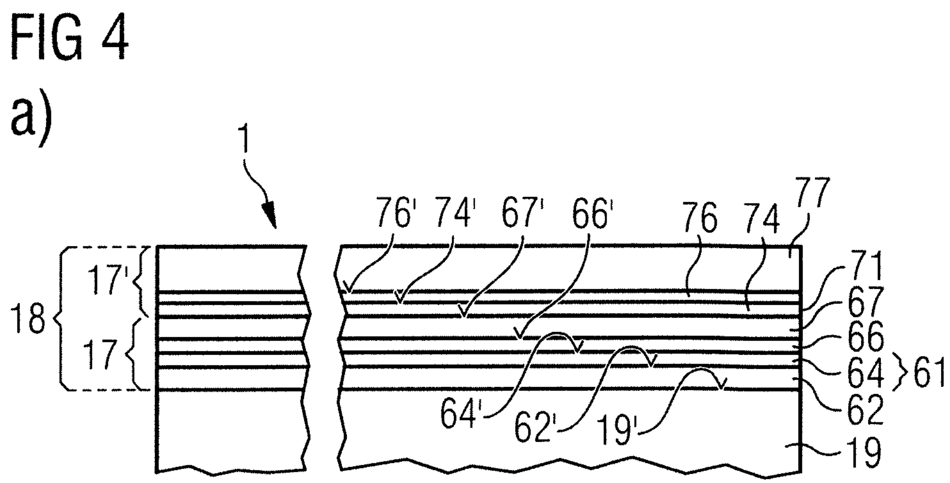
Figure 4:
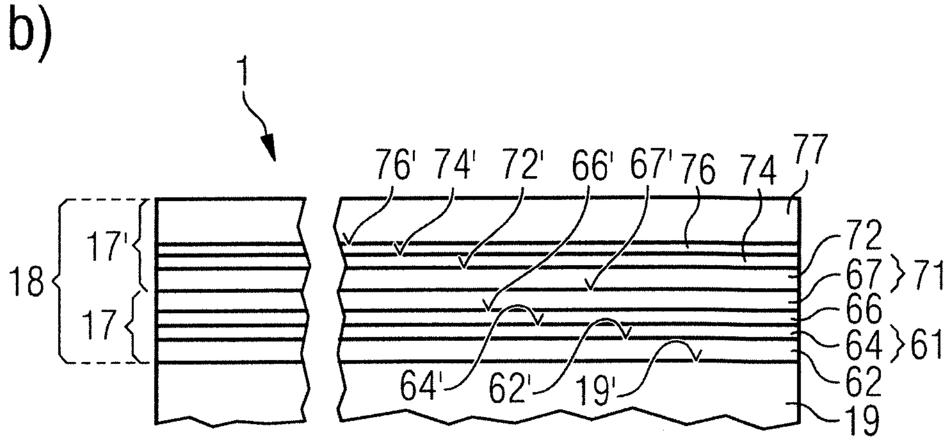
Figure 5:
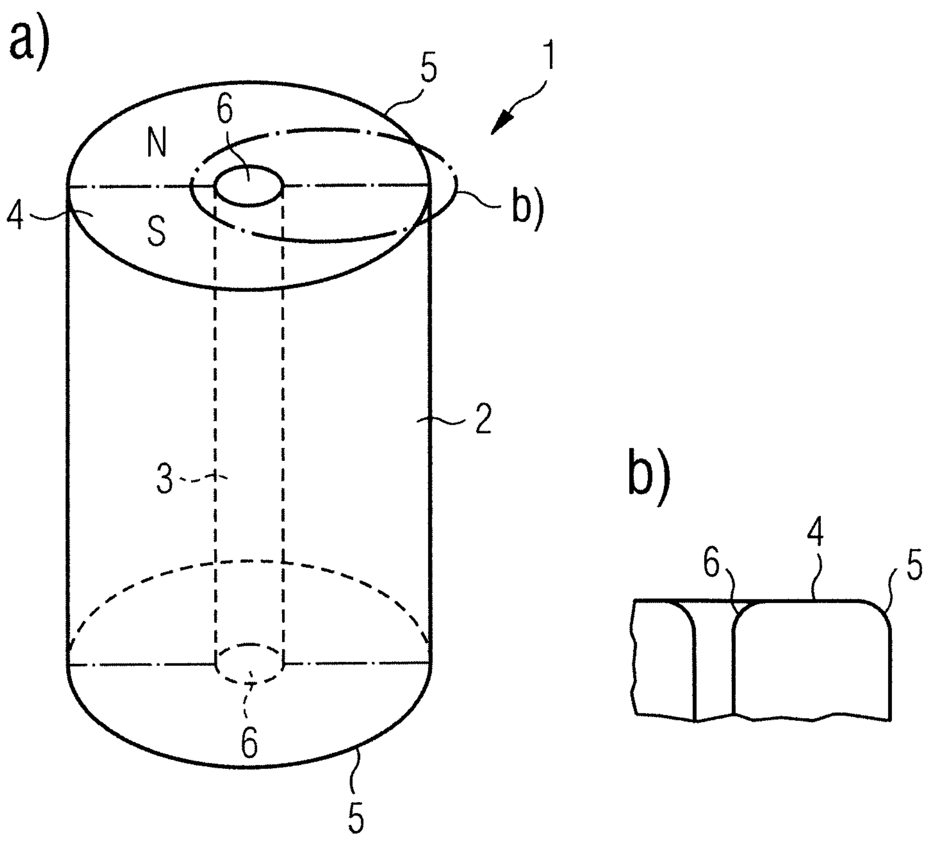
Figure 6:
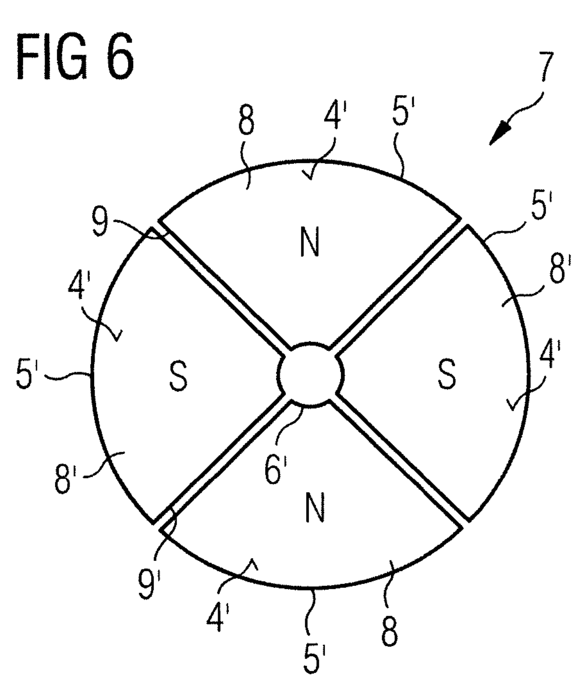

FIG. 2 is a schematic sectional view of a portion of a magnet according to the first embodiment of the present invention, FIG. 3*a* is a schematic sectional view of a portion of a magnet according to the second embodiment of the present invention, FIG. 3*b* is a schematic sectional view of a portion of another magnet according to the second embodiment of the present invention, FIG. 4*a* is a schematic sectional view of a portion of a magnet according to the third embodiment of the present invention, FIG. 4*b* is a schematic sectional view of a portion of another magnet according to the third embodiment of the present invention, FIG. 5*a* is a schematic representation of an exemplary single-piece magnet according to the present invention, FIG. 5*b* is a partial sectional view showing a detail of the magnet illustrated in FIG. 5*a*, and FIG. 6 is a schematic top view of an exemplary segmented magnet according to the present invention.

The drawings are not to scale. They should not be construed as limiting the invention in any manner.

The intravascular blood pump 10 illustrated in FIG. 1 has been described above. The pump is conventional in construction, but comprises a corrosion resistant permanent magnet 1 according to the present invention.

In the pump of FIG. 1, the magnet 1 is rod-shaped, the opposing front faces being flat and parallel to each other. While the composite coating according to the present invention may effectively protect a magnet body having sharp edges as illustrated in FIG. 1 against corrosion over an extended period of time, it is preferred in the present invention to use a magnet body having a shape as illustrated in FIGS. 5 and 6. The individual layers of the composite coating completely extend over each previously applied composite coating layer.

FIG. 2 is a schematic sectional view of a portion of a magnet 1 having a composite coating 15 according to the first embodiment of the present invention. In the case of the exemplary magnet illustrated in FIG. 2, the composite coating 15 is formed on a surface 19' of a non-magnetized magnet body 19. Composite coating 15 comprises a first aluminum oxide layer 42 formed by atomic layer deposition on surface 19' of magnet body 19. An aluminum layer 43 is deposited by physical vapor deposition on surface 42' of aluminum oxide layer 42. A second aluminum oxide layer 44 is deposited by atomic layer deposition on surface 43' of aluminum layer 43. The first aluminum oxide layer 42, the aluminum layer 43 and the second aluminum oxide layer 44, in combination, constitute the inorganic layer 41 of composite coating 15. A linker layer 46 is formed on surface 44' of the second aluminum oxide layer 44, and firmly bonds the organic layer 47 to the second metal oxide layer 44. The organic layer 47 of composite coating 15 consists of Parylene C and covers surface 46' of the linker layer 46.

In the case of the exemplary magnet illustrated in FIG. 2, the first aluminum oxide layer and the second aluminum oxide layer each have a thickness of 100 nm, the aluminum layer has a thickness of 4 μm, the layer formed from Parylene C has a thickness of 15 μm, and the linker layer is a monolayer.

FIG. 3*a* is a schematic sectional view of a portion of a magnet 1 having a composite coating 16 according to the second embodiment of the invention. In the case of the exemplary magnet illustrated in FIG. 3*a*, the composite coating 16 is formed on surface 19' of a non-magnetized magnet body 19. Composite coating 16 comprises a first metal oxide layer 52 consisting of titanium oxide. The first metal oxide layer 52 is deposited by atomic layer deposition on a surface 19' of the magnet body 19 to a thickness of 100 nm. A metal layer 53 consisting of titanium is deposited by physical vapor deposition on surface 52' of the first metal oxide layer 52 to a thickness of 4 μm. On surface 53' of metal layer 53, a second metal oxide layer 54 is deposited by atomic layer deposition to a thickness of 100 nm. The second metal oxide layer consists of a mixture of aluminum oxide and titanium oxide. A plating layer 55 is provided on a surface 54' of the second metal oxide layer 54. The plating layer 55 is an aluminum metal layer and has a thickness of about 15 μm. The first metal oxide layer 52, the metal layer 53, the second metal oxide layer 54 and the further metal layer 55, in combination, constitute an inorganic layer 51. A linker layer 56 is formed on surface 55' of the further metal layer 55, and firmly bonds the organic layer 57 to the further metal layer 55. The organic layer 57 of composite coating 16 consists of Parylene C and covers surface 56' of linker layer 56.

FIG. 3*b* shows a magnet 1 similar to the magnet shown in FIG. 3*a*, however, with a further metal oxide layer 58 provided on aluminum metal layer 55. In the embodiment illustrated in FIG. 3*b*, the further metal oxide layer 58 is a native aluminum oxide layer having a thickness of approximately 3 nm, i.e. a passivation layer formed upon exposure of the aluminum metal layer to air.

FIG. 4*a* is a schematic sectional view of a portion of a magnet 1 having a composite coating 18 according the third embodiment of the invention. In the case of the exemplary magnet illustrated in FIG. 4*a*, the composite coating 18 comprises a first layer structure 17 and a second layer structure 17'.

The first layer structure 17 comprises an inorganic layer 61 consisting of a first metal oxide layer 62 and a second metal oxide layer 64, an organic layer 67, and a linker layer 66 provided between the second metal oxide layer 64 and the organic layer 67. The second layer structure 17' is provided on the first layer structure 17, and comprises an inorganic layer 71 consisting of a third metal oxide layer 74, an organic layer 77 and a linker layer 76 provided between the third metal oxide layer 74 and the organic layer 77.

The first metal oxide layer is an aluminum oxide layer having a thickness of 100 nm, formed by atomic layer deposition on surface 19' of magnet body 19. The second metal oxide layer is a titanium oxide layer having a thickness of 10 nm, formed by atomic layer deposition on surface 62' of the first metal oxide layer. Linker layer 66 is a monolayer formed on surface 64' of the second metal oxide layer, and organic layer 67 is a layer formed from Parylene C on surface 66' of linker layer 66. The Parylene C layer has a thickness in a range from 1 to 2 μm.

The third metal oxide layer 74 is a titanium oxide layer having a thickness of 10 nm, formed by atomic layer deposition on surface 67' of the first organic layer 67. A linker layer 76 is provided on surface 74' of the titanium oxide layer, and a further Parylene C layer 77 is formed on surface 76' of linker layer 76. This outermost Parylene C layer has a thickness of about 13 μm.

FIG. 4*b* shows a magnet 1 similar to the magnet shown in FIG. 4*a*, however, an additional (intermediate) metal oxide layer 72 is provided between organic layer 67 and third metal oxide layer 74. Therefore, the second layer structure 17' comprises an inorganic layer 71 consisting of the intermediate metal oxide layer 72 and a third metal oxide layer 74, an organic layer 77 and a linker layer 76 provided between the third metal oxide layer 74 and the organic layer 77. The intermediate metal oxide layer 72 is an aluminum oxide layer having a thickness of 20 nm, formed by atomic layer deposition. As for the rest, the same applies as in the case of the embodiment illustrated in FIG. 4*a* above. The first layer structure and the second layer structure comprise layers made from the same materials (while in other embodiments, the materials may be different), but having different thicknesses.

In the embodiments illustrated in FIGS. 4*a* and 4*b* all linker layers are monolayers and are identical.

FIG. 5*a* shows a single-piece magnet 1 having a rod shape and a bore or channel extending therethrough in a longitudinal direction. During use of the magnet in an intravascular blood pump 10 as illustrated in FIG. 1, the channel receives the motor shaft 25. The opposing front faces 4 of the magnet are tapered towards the channel. The magnet 1 is provided with a composite coating according to the invention at the outer surfaces 2 exposed to the fluid flowing in gap 26 and the tapered front faces 4. The inner surfaces 3 adjacent to the motor shaft 25 may or may not be coated. Edge 5 at the transition between the outer surface 2 and the front surface 4, as well as edge 6 at the transition between front surface 4 and the inner surface 3, are coated. The edges are soft, thus facilitating the formation of a well-adhering uniform coating. “N” and “S” indicate the north pole and the south pole of the magnet.

FIG. 5*b* is a partial sectional view along the dash-dot line in FIG. 5*a*. FIG. 5*b* shows the region of the magnet within the loop in FIG. 5*a*. FIG. 5*b* clearly shows the soft edges 5, 6.

FIG. 6 shows a segmented magnet 7. The magnet illustrated in FIG. 6 has four segments 8, 8'. Segments 8, which are opposite to one another, have the same magnetic polarity, as indicated by “N” in the top view of FIG. 6, and segments 8', which are also opposite to one another, have the same magnetic polarity, as indicated by “S” in the top view of FIG. 6. As a result, adjacent segments 8, 8' have opposite magnetic polarity.

Segments 8, 8' have, analogously to the single-piece magnet shown in FIG. 5, inner surfaces, outer surfaces, opposing front faces, edges at the transition between the outer surfaces and the front surfaces, and edges at the transition between the front surfaces and the inner surfaces. The front faces are designated 4', and the edges are designated 5' and 6', respectively, in correspondence to the designations in FIG. 5. In addition, segments 8, 8' have side surfaces 9, 9', separated by gaps in the drawing. Of course, when the magnet is in use, side surfaces 9, 9' contact each other. All surfaces of each segment of the magnet may be completely covered by the inventive composite coating, but side surfaces 9, 9' which are not exposed because they contact each other, and the inner surfaces which are not exposed because they contact the motor shaft, do not need to be coated. Preferably all edges of all segments are soft edges.

Identical cylindrical non-magnetized $Nd_2Fe_{14}B$ sintered magnet bodies having a length of 12 mm and a diameter of 2.8 mm were coated (after washing, but without removal of the phosphate coating) with different coatings, magnetized, and subjected to corrosion testing in an aqueous solution containing 0.9 weight % sodium chloride at 60° C. In this test corrosion proceeds about 3.75 times faster than at room temperature in a solution of 5% to 40%, by weight, glucose in water for injection.

The following coatings proved to be particularly advantageous as regards the desired combination of excellent corrosion resistance and minimum rate of rejects:

Magnets according to the first embodiment having a first metal oxide layer and a second metal oxide layer formed by ALD to a thickness of 100 nm, a metal layer formed by PVD to a thickness of 4 μm, and a Parylene C coating formed to a thickness of 15±2 μm. The best magnets had (a) $Al_2O_3$ as a first and a second metal oxide layer and aluminum as a metal layer, (b) $Al_2O_3$ as a first and a second metal oxide layer and titanium as a metal layer, (c) $TiO_2$ as a first and a second metal oxide layer, and titanium as a metal layer, (d) $Al_2O_3$ as a first metal oxide layer, a mixture of $Al_2O_3$ and $TiO_2$ as a second metal oxide layer, and titanium as a metal layer, and (e) $TiO_2$ as a first metal oxide layer, a mixture of $Al_2O_3$ and $TiO_2$ as a second metal oxide layer, and titanium as a metal layer. Biasing during PVD appeared to improve coating quality.

Magnets according to the second embodiment having a first metal oxide layer formed by ALD to a thickness of 100 nm, a second metal oxide layer formed by ALD to a thickness of 100 nm, a metal layer formed by PVD to a thickness of 4 μm, a further metal layer (aluminum) formed by plating to a thickness of 15 μm±3 μm, and a Parylene C coating formed to a thickness of 15±2 μm.

The best magnets had (a) $Al_2O_3$ as the first metal oxide layer and the second metal oxide layer, and aluminum as the metal layer, (b) $TiO_2$ as the first metal oxide layer, a mixture of $Al_2O_3$ and $TiO_2$ as the second metal oxide layer, and titanium as the metal layer, and (c) $TiO_2$ as the first and the second metal oxide layer, and iron as the metal layer.

Magnets according to the third embodiment having $Al_2O_3$ as the first metal oxide layer, formed by ALD to a thickness of 100 nm, $TiO_2$ as the second metal oxide layer, formed by ALD to a thickness of 10 nm, a Parylene C coating formed to a thickness of 1 to 2 μm, $Al_2O_3$ as the intermediate metal oxide layer, formed by ALD to a thickness of 20 nm, $TiO_2$ as the third metal oxide layer formed by ALD to a thickness of 10 nm, and a Parylene C coating formed to a thickness of 13±2 μm.

In each case, linker layers and further linker layers, where applicable, were formed from an alcoholic solution (water/ethanol; acetic acid to achieve a pH of about 5 to 6; concentration of silane about 1%; reaction time about 5 minutes) containing silane A-174. Evaporation of the alcohol yielded essentially monolayers. Parylene C coatings were formed by plasma deposition.

The invention claimed is:

1. A corrosion-resistant permanent magnet comprising a magnet body and a composite coating provided on and covering surfaces of the magnet body, the composite coating comprising, in the order recited, a first metal oxide layer in physical contact with the magnet body, wherein a thickness of the first metal oxide layer is in a range from 80 nm to 120 nm;

a metal layer;

a second metal oxide layer;

a linker layer; and a layer formed from poly(2-chloro-p-xylylene).

2. The corrosion-resistant permanent magnet of claim 1, wherein the magnet body is a rare earth metal iron boron permanent magnet.

3. The corrosion-resistant permanent magnet of claim 2, wherein the magnet body is a sintered magnet body having $Nd_2Fe_{14}B$ crystals and a neodymium iron boron material surrounding the $Nd_2Fe_{14}B$ crystals, said neodymium iron boron material being richer in neodymium than the $Nd_2Fe_{14}B$ crystals.

4. The corrosion-resistant permanent magnet of claim 1, wherein the metal of the metal layer is aluminum or titanium or an alloy of aluminum or titanium.

5. The corrosion-resistant permanent magnet of claim 1, wherein the oxide of the first metal oxide layer is $Al_2O_3$ or $TiO_2$ or a mixed oxide of $Al_2O_3$ and $TiO_2$.

6. The corrosion-resistant permanent magnet of claim 1, wherein the oxide of the second metal oxide layer is $Al_2O_3$ or $TiO_2$ or a mixed oxide of $Al_2O_3$ and $TiO_2$.

7. The corrosion-resistant permanent magnet of claim 1, comprising a further metal layer and, optionally, a further metal oxide layer between the second metal oxide layer and the linker layer, wherein the metal layer is in physical contact with the first metal oxide layer, the second metal oxide layer is in physical contact with the metal layer, the further metal layer is in physical contact with the second metal oxide layer, the further metal oxide layer, if present, is in physical contact with the further metal layer, the linker layer is in physical contact with the further metal layer or, if present, the further metal oxide layer, and the layer formed from poly(2-chloro-p-xylylene) is in physical contact with the linker layer.

8. The corrosion-resistant permanent magnet of claim 7, wherein the metal of the further metal layer is aluminum.

9. The corrosion-resistant permanent magnet of claim 1, wherein the metal layer is omitted, and the composite coating further comprises, in the order recited, on the layer formed from poly(2-chloro-p-xylylene), a third metal oxide layer;

a further linker layer; and a further layer formed from poly(2-chloro-p-xylylene).

10. The corrosion-resistant permanent magnet of claim 9, wherein the oxide of the first metal oxide layer is $Al_2O_3$ and the oxide of the second metal oxide layer is $TiO_2$, or the oxide of the first metal oxide layer is $TiO_2$ and the oxide of the second metal oxide layer is $Al_2O_3$, or the oxides of the first and second metal oxide layers are $Al_2O_3$, or the oxides of the first and second metal oxide layers are $TiO_2$, and/or wherein the oxide of the third metal oxide layer is $TiO_2$ or $Al_2O_3$.

11. The corrosion-resistant permanent magnet of claim 9, further comprising an intermediate metal oxide layer between the layer formed from poly(2-chloro-p-xylylene) and the third metal oxide layer.

12. The corrosion-resistant permanent magnet of claim 11, wherein the oxide of the intermediate metal oxide layer is $Al_2O_3$ or $TiO_2$, and is different from the oxide of the third metal oxide layer.

13. An intravascular blood pump comprising an electric motor, wherein the electric motor comprises the corrosion-resistant permanent magnet of claim 1.

14. The corrosion-resistant permanent magnet of claim 1, wherein the thickness of the first metal oxide layer is 100 nm.

* * * * *